US010155842B2

(12) United States Patent
Duquenne et al.

(10) Patent No.: US 10,155,842 B2
(45) Date of Patent: Dec. 18, 2018

(54) TITANIUM-BASED CATALYST FOR VITRIMER RESINS OF EPOXY/ANHYDRIDE TYPE

(71) Applicants: ARKEMA FRANCE, Colombes (FR); CENTRE NATIONAL DE LA RECHERCHE SCIENTIFIQUE, Paris (FR); ECOLE SUPERIEURE DE PHYSIQUE ET DE CHIMIE INDUSTRIELLES DE LA VILLE DE PARIS, Paris (FR)

(72) Inventors: Christophe Duquenne, Paris (FR); Sebastien-Jun Mougnier, Paris (FR); Francois-Genes Tournilhac, Paris (FR); Ludwik Leibler, Paris (FR)

(73) Assignees: ARKEMA FRANCE, Colombes (FR); CENTRE NATIONAL DE LA RECHERCHE SCIENTIFIQUE, Paris (FR); ECOLE SUPERIEURE DE PHYSIQUE ET DE CHIMIE INDUSTRIELLES DE LA VILLE DE PARIS, Paris (FR)

( * ) Notice: Subject to any disclaimer, the term of this patent is extended or adjusted under 35 U.S.C. 154(b) by 0 days.

(21) Appl. No.: 15/306,000

(22) PCT Filed: Apr. 23, 2015

(86) PCT No.: PCT/FR2015/051109
§ 371 (c)(1),
(2) Date: Oct. 21, 2016

(87) PCT Pub. No.: WO2015/162387
PCT Pub. Date: Oct. 29, 2015

(65) Prior Publication Data
US 2017/0044307 A1 Feb. 16, 2017

(30) Foreign Application Priority Data

Apr. 24, 2014 (FR) .................................... 14 53677

(51) Int. Cl.
*C08G 59/68* (2006.01)
*C08G 59/42* (2006.01)
*C07F 7/28* (2006.01)

(52) U.S. Cl.
CPC .............. *C08G 59/683* (2013.01); *C07F 7/28* (2013.01); *C08G 59/42* (2013.01); *C08G 59/681* (2013.01); *C08G 59/682* (2013.01); *C08G 59/685* (2013.01)

(58) Field of Classification Search
CPC ..... C08G 59/682; C08G 59/685; C08G 59/70
See application file for complete search history.

(56) References Cited

U.S. PATENT DOCUMENTS

| 3,692,715 | A | 9/1972 | Groff |
| 4,137,275 | A | 1/1979 | Smith |
| 5,712,331 | A * | 1/1998 | Ryang ................ C08G 59/5066 523/400 |
| 9,266,292 | B2 | 2/2016 | Leibler |
| 9,359,467 | B2 | 6/2016 | Leibler |
| 2013/0300020 | A1 | 11/2013 | Leibler |

FOREIGN PATENT DOCUMENTS

| EP | 0758662 | 2/1997 |
| EP | 0810249 | 12/1997 |
| FR | 1419754 | 12/1965 |
| FR | 2584412 | 1/1987 |
| GB | 1069439 | * 5/1967 |
| WO | 9723516 | 7/1997 |
| WO | 2011151584 | 12/2011 |
| WO | 2012101078 | 8/2012 |
| WO | 2012152859 | 11/2012 |

OTHER PUBLICATIONS

International Search Report and Written Opinion for International Application No. PCT/FR2015/051109, dated Jun. 21, 2016, 28 pages.
"Epoxy Polymer" edited by J.P. Pascault and R.J.J. Williams, Wiley-VCH, Weinheim 2010, 13 pages.

* cited by examiner

Primary Examiner — Kuo Liang Peng
(74) Attorney, Agent, or Firm — RatnerPrestia

(57) ABSTRACT

The present invention relates to a composition containing, besides a thermosetting resin of epoxy type and a hardener of anhydride type, at least one catalyst comprising an organometallic titanium complex. This composition enables the manufacture of vitrimer resins, that is to say resins that can be deformed in the thermoset state. It also relates to a kit for manufacturing this composition, an object obtained from this composition and a kit for manufacturing this object. Another subject of the invention relates to an organometallic titanium complex corresponding to the structure titanium bis(3-phenoxy-1,2-propane dioxide) (Ti(PPD)$_2$), and the use thereof as vitrimer effect catalyst in systems based on epoxy resin and on hardener of anhydride type.

22 Claims, 4 Drawing Sheets

TITANIUM-BASED CATALYST FOR VITRIMER RESINS OF EPOXY/ANHYDRIDE TYPE

CROSS-REFERENCE TO RELATED APPLICATIONS

This is the national phase of International Application No. PCT/FR2015/051109, filed 23 Apr. 2015, which claims priority from French Application No. 1453677, filed 24 Apr. 2014. The disclosure of each of these applications is incorporated herein by reference in its entirety for all purposes.

FIELD OF THE INVENTION

The present invention relates to a composition containing, in addition to a thermosetting resin of epoxy type and a curing agent of anhydride type, at least one catalyst comprising an organometallic titanium complex. This composition allows the production of vitrimer resins, that is to say of resins that can be deformed in the thermoset state.

TECHNICAL BACKGROUND

Thermoset resins (or thermosets) have the advantage of having a high mechanical strength and a high thermal and chemical resistance and, for this reason, can replace metals in certain applications. They have the advantage of being lighter than metals. They can also be used as matrices in composite materials, as adhesives, and as coatings. Among the thermoset polymers, mention may be made of unsaturated polyesters, phenoplasts, polyepoxides, polyurethanes and aminoplasts.

Conventional thermosetting resins must be processed; in particular, they must be molded so as to immediately obtain the shape appropriate for the final use. This is because transformation is no longer possible once the resin is polymerized, other than machining which often remains difficult. Soft or hard parts and composites based on thermosetting resins can neither be transformed nor shaped; they cannot be recycled or welded.

In parallel to thermosetting resins, a class of polymer materials, thermoplastics, has been developed. Thermoplastics can be formed at high temperature by molding or by injection-molding, but have mechanical and thermal and chemical resistance properties that are less advantageous than those of thermoset resins.

In addition, the forming of thermoplastics can only be carried out in very narrow temperature ranges. This is because, when they are heated, thermoplastics become liquids, the fluidity of which varies abruptly in the region of the melting points and glass transition temperatures, thereby making it impossible to apply to them a whole variety of transformation methods that exist for glass and for metals for example.

In this context, vitrimer resins have been designed for the purpose of allying the advantages of both thermosets and thermoplastics. These materials have both the mechanical and solvent-resistance properties of thermoset resins and the capacity to be reshaped and/or repaired of thermoplastic materials. These polymer materials which are capable of indefinitely going from a solid state to a viscoelastic liquid, like glass, have been denoted "vitrimers". Contrary to thermoplastics, the viscosity of vitrimers varies slowly with temperature, thereby making it possible to use them for the production of objects that have specific shapes incompatible with a molding process, without using a mold or precisely controlling the forming temperature.

The specific properties of vitrimers are linked to the capacity of their network to reorganize above a certain temperature, without modifying the number of intramolecular bonds or depolymerizing, under the effect of internal exchange reactions. These reactions lead to a relaxing of the stresses within the material which becomes malleable, while preserving its integrity and remaining insoluble in any solvent. These reactions are made possible by the presence of a catalyst. In the case of vitrimers of epoxy-anhydride type, it has been suggested to use as catalyst a zinc, tin, magnesium, cobalt, calcium, titanium or zirconium metal salt, preferably zinc acetylacetonate (WO 2012/101078). Likewise, various catalysts have been suggested for use in hybrid thermoset/supramolecular systems obtained from a thermosetting resin, from a curing agent of anhydride-type or preferably of acid type and from a compound comprising an associative group and a function allowing grafting thereof onto the thermosetting resin (WO 2012/152859). These catalysts can be based on various metals, including titanium, and are in the form of various salts, in particular of alkoxides (or alcoholates) such as titanium isopropoxide, although zinc acetylacetonate is, here again, preferred.

Titanic acid esters or titanic acid polymer esters have moreover been proposed in documents FR 1419754 and GB 1069439 for efficiently accelerating the curing, by polycarboxylic anhydrides, of cycloaliphatic polyepoxides in which at least one epoxide group is in a five-membered ring.

In addition, a catalyst system of titanium aryloxy type, in particular titanium phenolate, such as titanium catecholate, has been suggested in document FR 2584412 for facilitating the anionic polymerization of epoxide resins.

As it happens, the inventors have demonstrated that the stresses developed within the materials obtained for example from zinc acetylacetonate are less completely and less rapidly relaxed than within materials prepared from catalysts in the form of specific organometallic titanium complex. The latter thus exhibit better deformation properties, which are more compatible with an industrial thermoforming process, which requires very rapid deformation and relaxing of the stresses. In addition, contrary to the materials obtained from other titanium catalysts, this ability to deform is not obtained to the detriment of the crosslinking density, and therefore of the mechanical properties of the material.

Furthermore, another drawback of zinc acetylacetonate is the fact that at the temperatures (from 250 to 350° C.) required for transformation, this catalyst is not sufficiently stable, thereby causing gas to be given off during hot manipulations of the material, resulting in a loss of mass measured in particular by thermogravimetric analysis (TGA).

SUMMARY OF THE INVENTION

Definitions

The term "thermosetting" resin is intended to mean a monomer, oligomer, prepolymer, polymer or any macromolecule capable of being chemically crosslinked. It is more preferentially intended to mean a monomer, oligomer, prepolymer, polymer or any macromolecule capable of being chemically crosslinked when it is reacted with a curing agent (also called crosslinking agent) in the presence of an energy source, for example heat or radiation, and optionally of a catalyst.

The term "thermoset" resin or resin "in the thermoset state" is intended to mean a thermosetting resin chemically crosslinked such that its gel point is reached or exceeded. The term "gel point" is intended to mean the degree of crosslinking starting from which the resin is virtually no longer soluble in solvents. Any method conventionally used by those skilled in the art may be carried out in order to verify it. The test described in application WO 97/23516, page 20, may for example be carried out. For the purposes of the invention, a resin is considered to be thermoset provided that its gel content, that is to say the percentage of its residual mass after being placed in a solvent relative to its initial mass before being placed in a solvent, is greater than or equal to 75%.

The term "curing agent" denotes a crosslinking agent capable of crosslinking a thermosetting resin. It is in this case a generally polyfunctional compound, bearing reactive anhydride functions capable of reacting with reactive functions borne by the resin.

When reference is made to ranges, expressions of the type "ranging from . . . to . . . " include the limits of the range. Expressions of the type "between . . . and . . . " exclude the limits of the range.

The first subject of the invention is a composition comprising at least:
  a catalyst comprising, and preferably consisting of, an organometallic titanium complex,
  a thermosetting resin comprising at least one and advantageously several epoxide functions and optionally at least one and advantageously several free hydroxyl and/or ester functions, and a thermosetting-resin curing agent chosen from carboxylic acid anhydrides.

According to the invention, the organometallic titanium complex is chosen from titanium alkoxides, titanium diketones, such as titanium acetylacetonate, and titanium carboxylates derived from carboxylic acids of formula R'COOH with R' denoting a linear or branched, saturated or unsaturated alkyl chain comprising from 1 to 24 carbon atoms.

The term "titanium alkoxide" denotes titanium compounds comprising a titanium atom linked to four alkoxide groups —OR, where:
  either each of the R groups independently denotes a linear or branched, saturated or unsaturated, preferably saturated, hydrocarbon-based chain having from 1 to 20 carbon atoms, which is optionally interrupted with one or more hetero atoms chosen from N, O, S and P, and optionally interrupted or terminated with one or more saturated, partially unsaturated or totally unsaturated hydrocarbon-based rings,
  or each pair of adjacent R groups forms, with the titanium, a saturated or unsaturated, preferably saturated, ring comprising from 5 to 7 members, which is optionally substituted with a hydrocarbon-based chain as defined above.

It is understood that the term alkoxide does not include phenates.

The thermosetting resin in the composition according to the invention is chosen from the family of glycidyl esters, glycidyl ethers, glycidyl amines and glycidyl isocyanurates, comprising at least two glycidyl groups per molecule, or from epoxidized olefin compounds which are linear, branched or cyclic comprising more than six members.

The above catalyst may be denoted "vitrimer effect catalyst" in the remainder of the description. The vitrimer effect catalyst facilitates the internal exchange reactions within a thermoset resin so as to make it deformable.

It is understood that the above catalyst is present, in the composition of the invention, in addition to the catalysts that may already be present intrinsically in the thermosetting resin and/or in the curing agent, due to the fact that the preparation thereof can be carried out in the presence of catalysts in a low content, and in addition to the conventional catalysts for curing epoxy resins with anhydrides, that are optionally present.

It is understood that the composition does not comprise any compound comprising an associative group and a function allowing the grafting thereof onto the thermosetting resin.

It is understood that the composition of the invention does not comprise any thermosetting resin of cycloaliphatic polyepoxide type having at least one 1,2-epoxide group which is in a five-membered ring.

The invention also relates to the compound titanium bis(3-phenoxy-1,2-propane dioxide), denoted herein as "Ti(PPD)$_2$", which is a specific organometallic titanium complex, and to the use thereof as a vitrimer effect catalyst in systems based on an epoxy resin and on a curing agent of anhydride type.

Another subject of the invention is a composition comprising at least one thermosetting resin chosen from the family of glycidyl esters, glycidyl ethers, glycidyl amines and glycidyl isocyanurates, comprising at least two glycidyl groups per molecule, or from epoxidized olefin compounds which are linear, branched or cyclic comprising more than six members, at least one carboxylic acid anhydride and at least titanium bis(3-phenoxy-1,2-propane dioxide) Ti(PPD)$_2$.

Another subject of the invention is a composition comprising at least one thermosetting resin chosen from bisphenol A diglycidyl ether (DGEBA), tetraglycidyl methylene dianiline (TGMDA), Novolac resins, and glycidyl methacrylate, preferably at least one bisphenol A diglycidyl ether, and at least one carboxylic acid anhydride, and at least titanium bis(3-phenoxy-1,2-propane dioxide) Ti(PPD)$_2$.

A subject of the invention is also a kit for producing a composition according to the invention, comprising at least:
  a first composition comprising the catalyst, alone or with the curing agent or the thermosetting resin;
  optionally a second composition comprising the curing agent;
  optionally a third composition comprising the thermosetting resin.

Another subject of the invention is the use of the above-mentioned composition for producing an object made of thermoset resin that is hot-deformable, and also an object comprising a thermoset resin obtained from the composition according to the invention.

Another subject of the invention is a process for deforming an object as defined above, such as an assembly, welding, repairing or recycling process, comprising the application, to this object, of a mechanical stress at a temperature (T) above the glass transition temperature Tg of the thermoset resin.

Finally, a subject of the invention is the use of one or more objects as described above in the motor vehicle, aeronautical, nautical, aerospace, sport, construction, electrical, electrical insulation, electronics, wind power, packaging and printing fields.

DETAILED DESCRIPTION

As indicated above, the composition according to the invention contains a catalyst comprising an organometallic titanium complex, preferably a titanium alkoxide.

Examples of titanium alkoxides are titanium propoxide, titanium isopropoxide, titanium butoxide and the compounds resulting from the reaction of these alkoxides with glycols, such as the compounds obtained according to the following reaction:

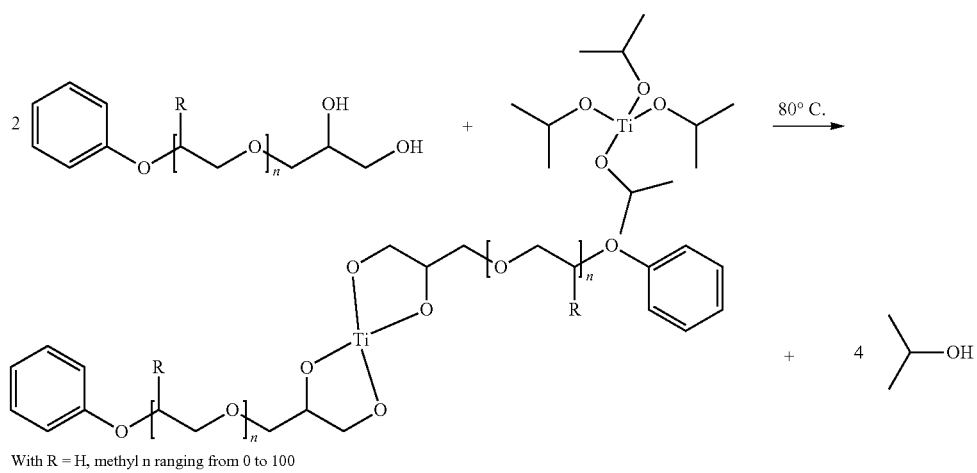

With R = H, methyl n ranging from 0 to 100

An organometallic titanium complex that is particularly advantageous as a vitrimer effect catalyst for the composition according to the invention is the compound titanium bis(3-phenoxy-1,2-propane dioxide), denoted herein as "Ti (PPD)$_2$", obtained with n=0, according to the following reaction:

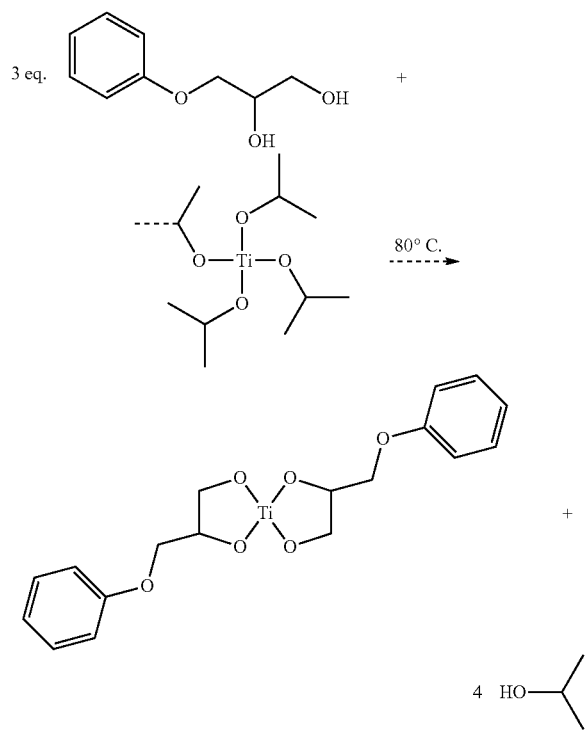

It is preferable to use, as titanium alkoxide, titanium isopropoxide Ti(iPr)$_4$ or titanium phenoxypropanediol Ti(PPD)$_2$ as illustrated in the above reaction.

According to one preferred form of the invention, the titanium complex comprises at least one chelating ligand as described.

The catalyst of organometallic titanium complex type comprising at least one chelating ligand may also be a titanium carboxylate derived from at least one carboxylic acid of formula R'COOH with R' denoting a linear or branched, saturated or unsaturated alkyl chain comprising from 1 to 24 carbon atoms.

As examples of carboxylic acids, mention may be made of fatty acids resulting from the hydrolysis of vegetable oils, 2-ethylhexanoic acid, benzoic acid and substituted derivatives thereof, salicylic acid, ricinoleic acid, 12-hydroxystearic acid, lactic acid, glycolic acid, acrylic acid and methacrylic acid. Phthalic acid, oxalic acid or succinic acid may also be suitable.

The catalyst of organometallic titanium complex type comprising at least one chelating ligand may also be chosen from titanium diketones such as titanium acetylacetonate.

According to one embodiment of the invention, the catalyst of organometallic titanium complex type is insoluble in the thermosetting resin and becomes soluble in the epoxy resin/anhydride system.

According to one embodiment of the invention, the catalyst of organometallic titanium complex type does not by itself initiate the anionic polymerization of the thermosetting resin. This characteristic is particularly advantageous for the vitrimer resins for which anionic ring-opening polymerization (ROP) is not desired since it generates chemical bonds of ether type which are not exchangeable by transesterification.

According to one preferred embodiment of the invention, the catalyst is titanium bis(3-phenoxy-1,2-propane dioxide).

According to one embodiment of the invention, the catalyst represents from 1 to 50 mol %, preferably from 2 to 25 mol %, more preferentially from 5 to 20 mol %, better still from 10 to 15 mol %, relative to the molar amount of epoxy functions in said thermosetting resin.

The composition according to the invention also comprises at least one curing agent of carboxylic acid anhydride type (comprising at least one —C(O)—O—C(O)— function).

The number of moles of titanium atoms can range from 1 to 50%, preferably from 2 to 25%, preferably from 5 to 20%, relative to the number of moles of anhydride functions of the curing agent.

As curing agents of anhydride type, mention may in particular be made of cyclic anhydrides, for instance phthalic anhydride, nadic or methylnadic anhydride, dodecenylsuccinic anhydride (DDSA), glutaric anhydride; partially or totally hydrogenated aromatic anhydrides such as tetrahydrophthalic anhydride, or methyltetrahydrophthalic anhydride, hexahydrophthalic anhydride or methylhexahydrophthalic anhydride; and mixtures thereof.

As curing agents of anhydride type, mention may also be made of succinic anhydride, maleic anhydride, trimellitic anhydride, the adduct of trimellitic anhydride and of ethylene glycol, chlorendic anhydride, tetrachlorophthalic anhydride, pyromellitic dianhydride (PMDA), 1,2,3,4 cyclopentanetetracarboxylic acid dianhydride, aliphatic acid polyanhydrides such as polyazelaic polyanhydride, polysebacic polyanhydride and mixtures thereof.

Use may in particular be made of the anhydrides having the following formulae, and mixtures thereof:

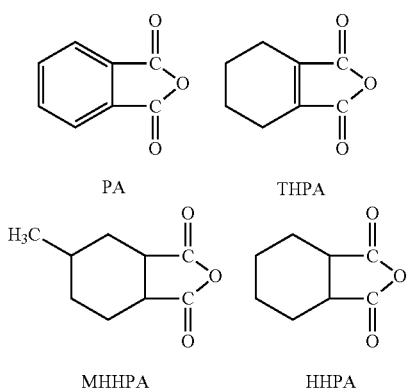

PA    THPA

MHHPA    HHPA

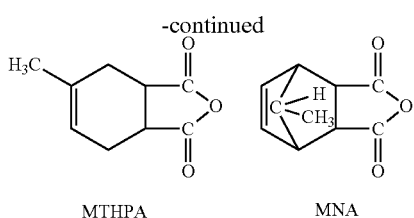

MTHPA    MNA and more preferentially MTHPA.

As curing agent of anhydride type, mention may also be made of the curing agent of commercial reference HY905 sold by Huntsman, which is a liquid mixture of several anhydrides.

Advantageously, the amount of curing agent is such that the number of moles of epoxide functions of the resin can range from 50 to 300%, preferably from 100% to 200%, preferably from 125 to 150%, relative to the number of moles of anhydride functions of the curing agent.

The composition according to the invention also comprises at least one thermosetting resin comprising at least one and advantageously at least several epoxide functions and optionally at least one and advantageously several free hydroxyl functions and/or ester functions, chosen from the family of glycidyl esters, glycidyl ethers, glycidyl amines and glycidyl isocyanurates, comprising at least two glycidyl groups per molecule, or from epoxidized olefin compounds which are linear, branched or cyclic comprising more than six members.

Such a resin will be denoted "epoxy resin".

The thermosetting resin according to the invention is chosen in particular so as to make it possible, after curing, to achieve a glass transition temperature (Tg) of between 60 and 170° C., preferably between 80 and 150° C., more preferentially between 100 and 140° C.

Advantageously, the epoxy resin represents at least 10% by weight, at least 20% by weight, at least 40% by weight, at least 60% by weight, or even 100% by weight, of the total weight of thermosetting resin present in the composition.

There are two major categories of epoxy resins: epoxy resins of glycidyl type, and epoxy resins of non-glycidyl type. The epoxy resins of glycidyl type are themselves categorized as glycidyl ether, glycidyl ester and glycidyl amine. The non-glycidyl epoxy resins are of aliphatic or cycloaliphatic type.

The glycidyl epoxy resins are prepared by means of a condensation reaction of a diol, diacid or diamine with epichlorohydrin. The non-glycidyl epoxy resins are formed by peroxidation of the olefinic double bonds of a polymer.

Among the glycidyl epoxy ethers, bisphenol A diglycidyl ether (DGEBA) represented below is most commonly used.

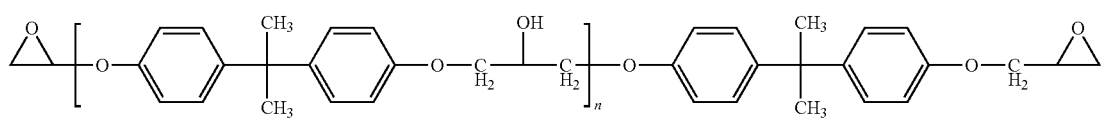

DGEBA-based resins have excellent electrical properties, low shrinkage, good adhesion on numerous metals, good moisture resistance, good resistance to mechanical impacts and good heat resistance.

The properties of DGEBA resins depend on the value of the degree of polymerization n, which itself depends on the stoichiometry of the synthesis reaction. Generally, n varies from 0 to 25.

Novolac epoxy resins (the formula of which is represented below) are glycidyl ethers of Novolac phenolic resins. They are obtained by reaction of phenol with formaldehyde in the presence of an acid catalyst so as to produce a Novolac phenolic resin, followed by a reaction with epichlorohydrin in the presence of sodium hydroxide as catalyst.

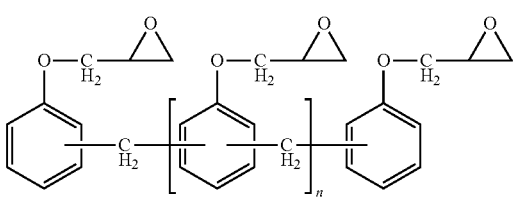

The Novolac epoxy resins generally contain several epoxide groups. The multiple epoxide groups make it possible to produce thermoset resins of high crosslinking density. The Novolac epoxy resins are widely used to produce materials for microelectronics because of their greater strength at a high temperature, their excellent molding ability, and their greater mechanical, electrical, heat-resistance and moisture-resistance properties.

The thermosetting resin that can be used in the present invention can for example be chosen from the family of glycidyl esters, glycidyl ethers, glycidyl amines and glycidyl isocyanurates, comprising at least two glycidyl groups per molecule, which comprises, without this list being exhaustive, Novolac epoxy resins, bisphenol A diglycidyl ether (DGEBA), hydrogenated bisphenol A diglycidyl ether, bisphenol F diglycidyl ether, tetraglycidyl methylene dianiline (TGMDA), pentaerythritol tetraglycidyl ether, trimethylol triglycidyl ether (TMPTGE), tetrabromo bisphenol A diglycidyl ether, or hydroquinone diglycidyl ether, ethylene glycol diglycidyl ether, propylene glycol diglycidyl ether, butylene glycol diglycidyl ether, neopentyl glycol diglycidyl ether, 1,4-butanediol diglycidyl ether, 1,6-hexanediol diglycidyl ether, cyclohexanedimethanol diglycidyl ether, polyethylene glycol diglycidyl ether, polypropylene glycol diglycidyl ether, polytetramethylene glycol diglycidyl ether, resorcinol diglycidyl ether, neopentyl glycol diglycidyl ether, bisphenol A polyethylene glycol diglycidyl ether, bisphenol A polypropylene glycol diglycidyl ether, the diglycidyl ester of phthalic, isophthalic or terephthalic acid, poly(glycidyl acrylate), poly(glycidyl methacrylate), versatic acid glycidyl esters, also known as diglycidyl ester of acid dimers, such as those sold under the name Cardura® E8, E10 or E12 by the company Momentive (Cardura® E10 with CAS 26761-45-5), castor oil polyglycidyl ether, triglycidyl isocyanurate (TGIC), and mixtures thereof.

The thermosetting resin that can be used in the present invention can also be chosen from epoxidized olefin compounds which are linear, branched or cyclic comprising more than six members, comprising, without this list being exhaustive, epoxidized polyunsaturated fatty acids, epoxidized vegetable oils, in particular epoxidized soybean oil, epoxidized fish oils and epoxidized limonene; the epoxidized cycloaliphatic resins sold under the name Araldite® CY179, CY184, MY0510 and MY720 by the company BASF, and the CY179 and CY184 resins corresponding respectively to the formulae below:

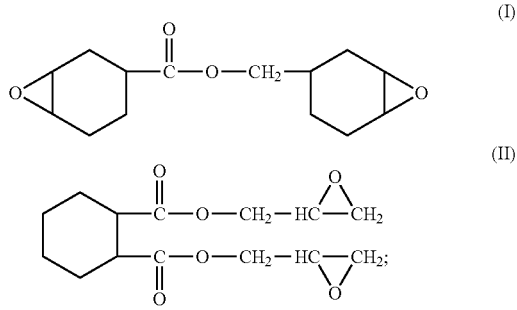

The thermosetting resin that can be used in the present invention can also be chosen from monoepoxide compounds such as glycidyl methacrylate, alkoxylated glycidyl (meth) acrylates; $C_8$-$C_{10}$ alkyl glycidyl ethers, $C_{12}$-$C_{14}$ alkyl glycidyl ethers, neodecanoic acid glycidyl ester, butyl glycidyl ether, cresyl glycidyl ether, phenyl glycidyl ether, p-nonyl-phenyl glycidyl ether, p-nonylphenyl glycidyl ether, p-t-butyl phenyl glycidyl ether, 2-ethylhexyl glycidyl ether, and mixtures thereof.

The composition according to the invention can comprise a mixture of the abovementioned epoxy resins.

According to one embodiment of the invention, the thermosetting resin is chosen from the family of glycidyl esters, glycidyl ethers, glycidyl amines and glycidyl isocyanurates, comprising at least two glycidyl groups per molecule.

According to one embodiment of the invention, the thermosetting resin is chosen from the family of epoxidized olefin compounds which are linear, branched or cyclic comprising more than six members.

According to one preferred embodiment of the invention, the thermosetting resin is chosen from: DGEBA, TGMDA, bisphenol F diglycidyl ether, Novolac resins, TMPTGE, the diglycidyl ester of phthalic, isophthalic or terephthalic acid, tetrabromo bisphenol A diglycidyl ether, 1,4-butanediol diglycidyl ether, Araldite®CY184 of formula (II) above, TGIC, poly(glycidyl methacrylate), and mixtures thereof.

According to one preferred embodiment of the invention, it is DGEBA, TGMDA, Novolac resins or glycidyl methacrylate.

According to one embodiment, the composition consists of the catalyst, the curing agent and a thermosetting epoxy resin, as defined above. According to this embodiment, the number of moles of titanium atoms can range from 1 to 50%, preferably from 2 to 25%, preferably from 5 to 20%, relative to the number of moles of anhydride functions. The number of moles of epoxide functions of the resin can range from 50 to 300%, preferably from 100 to 200%, preferably from 125 to 150%, relative to the number of moles of anhydride functions of the curing agent.

The composition of the invention can optionally comprise one or more additional compounds, insofar as their presence does not impair the advantageous properties which ensue from the invention. Examples of such additional compounds are: polymers, pigments, dyes, fillers, plasticizers, long or short, woven or nonwoven fibers, flame retardants, antioxidants, lubricants, wood, glass, metals, and mixtures thereof.

Advantageously, the content of thermosetting resin and of curing agent ranges from 10% to 90% by weight, in particular from 20% to 80% by weight or even from 30% to 70% by weight, relative to the total weight of the composition, the remainder to 100% being provided by the catalyst and optionally by additional compounds chosen from the abovementioned compounds.

Among the polymers that can be used as a mixture with the composition of the invention, mention may be made of: elastomers, thermoplastics, thermoplastic elastomers, and impact additives.

The term "pigment" is intended to mean colored particles that are insoluble in the composition of the invention. As pigments that can be used according to the invention, mention may be made of titanium oxide, carbon black, carbon nanotubes, metal particles, silica, metal oxides, metal sulfides or any other mineral pigment; mention may also be made of phthalocyanines, anthraquinones, quinacridones, dioxazines, azo pigments or any other organic pigment, natural pigments (madder, indigo, murex, cochineal, etc.) and pigment mixtures.

The term "dyes" is intended to mean molecules that are soluble in the composition of the invention and that have the ability to absorb a part of the visible radiation range.

Among the fillers that can be used in the composition of the invention, mention may be made of the fillers conventionally used in polymer formulations. Mention may be made, without this being limiting, of: silica, clays, carbon black, kaolin, talc, calcium carbonate, whiskers, and mixtures thereof.

Among the fibers that can be used in the composition of the invention, mention may be made of: glass fibers, carbon fibers, polyester fibers, polyamide fibers, aramid fibers, cellulose-based and nanocellulose-based fibers or else plant fibers (flax, hemp, sisal, bamboo, etc.), and mixtures thereof.

The presence, in the composition of the invention, of pigments, dyes or fibers capable of absorbing radiation, or mixtures thereof, can serve to perform the heating of a material or of an object produced from such a composition, by means of a radiation source such as a laser.

The presence, in the composition of the invention, of electricity-conducting pigments, fibers or fillers, such as carbon black, carbon nanotubes, carbon fibers, metal powders, magnetic particles, or mixtures thereof, can be used to perform the heating of a material or of an object produced from such a composition, by the Joule effect, by induction or by microwaves. Such heating can make it possible to carry out a process for producing, transforming or recycling a material or an object according to a process that will be described later.

The additional compounds can also be chosen from one or more other catalysts and/or curing agents, of any nature known to those skilled in the art as performing these roles insofar as they do not impair the advantageous properties which ensue from the invention. They will be denoted "additional catalyst" and "additional curing agent".

According to one preferred embodiment of the invention, the composition described herein also contains one or more additional catalysts which are specific for epoxide opening, such as:
  optionally blocked tertiary amines, for instance: 2,4,6-tris(dimethylaminomethyl)phenol (for example sold under the name Ancamine), o-(dimethylaminomethyl)phenol, benzyldimethylamine (BDMA), 1,4-diazabicyclo(2,2,2)octane (DABCO), methyltribenzylammonium chloride;
  imidazoles, such as 2-methylimidazole (2-MI), 2-phenylimidazole (2-PI), 2-ethyl-4-methylimidazole (EMI), 1-propylimidazole, 1-ethyl-3-methylimidazolium chloride, 1-(2-hydroxypropyl)imidazole;
  phosphoniums: tetraalkyl- and alkyltriphenylphosphonium halides;
  polyacid amine salts, aniline-formaldehyde condensates, N,N-alkanolamines, trialkanolamine borates, fluoroborates such as boron trifluoride monoethylamine (BF3-MEA), organosubstituted phosphines, quaternary monoimidazoline salts, mercaptans, polysulfides;
  and mixtures thereof.

Preferentially, the epoxide-opening catalyst is chosen from: tertiary amines, imidazoles, and mixtures thereof.

(Hetero)aromatic amines, such as 2-methylimidazole and tris(dimethylaminomethyl)phenol, are more particularly preferred as epoxide-opening catalyst for use in this invention.

This epoxide-opening additional catalyst is advantageously used in the composition in a proportion of from 0.1 mol % to 5 mol % relative to the number of moles of epoxide functions borne by the thermosetting resin.

Use may also be made of one or more vitrimer effect additional catalysts chosen from the catalysts mentioned in applications WO2011/151584, WO2012/101078 and WO 2012/152859, always insofar as their presence does not impair the advantageous properties which ensue from the invention.

The vitrimer effect additional catalyst can for example be present in the composition of the invention in a proportion of from 0.1 to 10% by weight and preferably from 0.1 to 5% by weight relative to the total weight of the composition.

Moreover, the use of an additional curing agent makes it possible to obtain, for the materials ultimately produced, a wide range of mechanical properties at ambient temperature (for example control of the glass transition temperature and/or of the modulus of a thermosetting resin).

As examples of additional curing agents, mention may be made of epoxy resin curing agents, in particular those chosen from amines, polyamides, polycarboxylic acids, phenolic resins, anhydrides (optionally other than those described above as acid curing agents), isocyanates, polymercaptans, dicyanodiamides, and mixtures thereof.

In particular, an additional curing agent of amine type can be chosen from primary or secondary amines having at least one $—NH_2$ function or two $—NH$ functions and from 2 to 40 carbon atoms. These amines can for example be chosen from aliphatic amines such as diethylenetriamine, triethylenetetramine, tetraethylenepentamine, dihexylenetriamine, cadaverine, putrescine, hexanediamine, spermine, isophorone diamine, and also aromatic amines such as phenylenediamine, diaminodiphenylmethane, diaminodiphenylsulfone, methylenebischlorodiethylaniline, metaxylylenediamine (MXDA) and hydrogenated derivatives thereof such as 1,3-bis(aminomethylcyclohexane) (1,3-BAC); and mixtures thereof. An additional curing agent of amine type can also be chosen from polyetheramines, for example the Jeffamines from Huntsman, optionally as mixtures with other additional curing agents.

As preferred additional curing agents, mention may be made of diethylenetriamine, triethylenetetramine, hexanediamine, and mixtures thereof.

According to one preferred embodiment of the invention, the composition described herein also contains at least one polyol, that is to say a compound comprising at least two hydroxyl functions, in particular a linear or branched polyhydroxyalkane, such as glycerol, trimethylolpropane or pentaerythritol, preferably glycerol. It has in fact been observed that the addition of this compound to the reaction mixture makes it possible to further improve the vitrimer properties of the material, that is to say to obtain a material capable of more completely and more rapidly relaxing the stresses after application of a deformation.

Process for Preparing the Composition

The compounds of the composition according to the invention are either commercially available, or can be easily synthesized by those skilled in the art starting from commercially available raw materials.

The composition of the invention can be obtained by simply bringing the compounds that it contains into contact. This bringing into contact is preferably carried out at a temperature ranging from 15° C. to 130° C., in particular from 50° C. to 125° C. The bringing into contact can be carried out with or without homogenization means.

According to one particular embodiment, the process comprises a first step during which the catalyst is pre-introduced into the resin or the curing agent, preferably into the curing agent. The catalyst can then be in the form of a dispersion if it is a powder, or a solution. This dispersion or dissolving can be carried out at ambient temperature or under hot conditions in order to obtain the desired viscosity characteristics.

According to another particular embodiment, the process comprises a first step of forming an activated species, comprising bringing the curing agent or the thermosetting resin into contact with the catalyst, so as to complex the titanium atom of the catalyst in the curing agent or the thermosetting resin.

Kits

The composition in accordance with the invention can be prepared from a kit comprising at least:
- a first composition comprising the catalyst, alone or with the curing agent or the thermosetting resin;
- optionally a second composition comprising the curing agent;
- optionally a third composition comprising the thermosetting resin.

It is also possible to provide for a kit for producing an object in accordance with the invention, comprising at least:
- a first composition comprising the catalyst, alone or with the curing agent or the thermosetting resin;
- optionally a second composition comprising the curing agent;
- optionally a third composition comprising the thermosetting resin.

The various compositions can be stored together or separately. It is also possible to store some of the compositions together, while at the same time keeping them separate from the other compositions.

The various compositions are generally stored at ambient temperature.

Preferably, when the second and third compositions are both present in the kit, they are in a packaging suitable for preventing a crosslinking reaction between the thermosetting resin and the curing agent from taking place without the intervention of an operator.

The packaging can consist of a container comprising two or even three internal compartments enabling separate storage of each of the compositions. According to one variant, the kit can consist of one single container, containing a mixture, in appropriate amounts, of the two or three compositions. In this latter case, the intervention of the operator is advantageously limited to heating.

It is possible to provide for a means for bringing the contents of the various compartments into contact, advantageously in such a way as to make it possible to initiate the crosslinking in the container.

It is also possible to provide for a kit consisting of several distinct bottles combined in the same packaging and each comprising the suitable amounts of each of the compositions for preparing the composition of the invention, so as to avoid the user having to perform weighing out and/or metering out operations.

Uses

The composition described above can be used for producing an object made of thermoset resin that is hot-deformable.

When the components of the present invention are mixed, it is thought, without wishing to be bound by this theory, that the catalyst opens the anhydride ring of the curing agent so as to form a monoester and a carboxylic acid which, subsequently, opens the epoxide ring of the thermosetting resin to form a diester and a free hydroxyl group. The thermoset resin obtained from the composition according to the invention is hot-deformable.

The term "hot-deformable" is intended to mean at a temperature (T) above the glass transition temperature Tg of the thermoset resin.

The thermoset resin obtained from the composition according to the invention advantageously has:
- a glass transition temperature (Tg) of between 60 and 170° C., preferably between 80 and 150° C., more preferentially between 100 and 140° C.,
- a relaxation time τ necessary for obtaining a normalized stress value equal to 1/e at a temperature equal to Tg+100° C. and/or to 200° C., which is less than 5000 seconds, preferably less than 2000 seconds, more preferentially less than 1000 seconds or even less than 500 seconds,
- a percentage of relaxed stresses after 5000 seconds at a temperature equal to Tg+100° C. and/or to 200° C., which is at least 80%, preferably at least 90%, more preferentially at least 95%, or even 100%,
- a storage modulus (G') at the rubbery plateau, for example at a temperature of between 150 and 200° C., that is greater than 5 MPa, preferably greater than or equal to 10 MPa, or even greater than or equal to 15 MPa.

These magnitudes are measured according to the protocols indicated in the examples hereinafter.

Objects and Processes for the Production Thereof

The invention also relates to an object comprising a thermoset resin obtained from at least one composition in accordance with the invention.

For the purposes of the present invention, the term "object" is intended to mean a three-dimensional part. Included in this definition are coatings, films, sheets, ribbons, etc. The objects according to the invention can in particular consist of coatings deposited on a support, such as a protective layer, a paint or else an adhesive film. Also included are powders, granules, etc.

The object according to the invention can be produced according to a production process comprising:
a) preparing or making available a composition in accordance with the invention,
b) forming the composition resulting from step a),
c) applying an energy enabling curing of the resin,
d) cooling the thermoset resin.

Steps a), b) and c) of the process may be successive or simultaneous.

The preparation of the composition can be carried out in a mixer of any type known to those skilled in the art. It can in particular be carried out by bringing the compositions described in relation to the kit into contact so as to form a composition according to the invention.

The forming can be carried out by any technique known to those skilled in the art in the field of thermosetting resins, in particular by molding. Notably, the invention makes it possible to also provide for other modes of forming, such as casting, filament coiling, continuous molding or molding between film coatings, infusion, pultrusion, resin transfer molding or RTM, reaction injection molding (or RIM) or any other methods known to those skilled in the art, as described in the works "Epoxy Polymer" edited by J. P. Pascault and R. J. J. Williams, Wiley-VCH, Weinheim 2010 or "Chimie industrielle" ["Industrial chemistry"], by R. Perrin and J. P. Scharff, Dunod, Paris 1999.

The forming can consist of placing in the form of a powder or of grains by any technique known to those skilled in the art. Mechanical milling may also be carried out at the end of step d).

With regard to the forming of the composition in coating form, use may advantageously be made of any method known in the art, in particular: the application of the composition with a brush or a roller; the dipping of a support to be coated in the composition; the application of the composition in the form of a powder.

If an attempt is made to form a composition of thermoset resin of the prior art in the same way as described above, the material or the object obtained is no longer deformable nor repairable nor recyclable once the gel point of the resin is reached or exceeded. The application of a moderate temperature to such an object according to the prior art does not result in any observable or measurable transformation, and the application of a very high temperature results in degradation of this object.

Conversely, the objects of the invention, because they are produced from a composition in accordance with the invention, can be deformed, welded, repaired and recycled via an increase in their temperature.

The expression "applying an energy enabling curing of the resin" is intended to mean generally a temperature increase. The applying of an energy enabling curing of the resin can for example consist of heating at a temperature ranging from 50 to 250° C., for example from 50 to 120° C. It is also possible to carry out an activation by radiation, for example by UV rays or an electron beam, or chemically, in particular by the radical route, for example by means of peroxides.

The cooling of the thermoset resin is usually carried out by leaving the material or the object to return to ambient temperature, with or without use of a cooling means.

An object in accordance with the invention may be composite. It may in particular result from the assembly of at least two objects, at least one of which, and advantageously both of which, comprise(s) at least one thermoset resin obtained from at least one composition in accordance with the invention.

It is for example a stratified material, comprising an alternating superposition of layers of thermoset resin obtained from at least one composition in accordance with the invention, with layers of wood, metal or glass.

An object of the invention may also comprise one or more additional components chosen from those mentioned above and in particular: polymers, pigments, dyes, fillers, plasticizers, long or short, woven or nonwoven fibers, flame retardants, antioxidants, lubricants, wood, glass and metals. When such an object is produced in accordance with one of the production processes described above, the additional compounds may be introduced before, during or after step a).

Deformation Process

The thermoset resins obtained as described herein have the advantage of exhibiting a slow variation in viscosity over a wide temperature range, which makes the behavior of an object of the invention comparable to that of inorganic glasses and makes it possible to apply thereto deformation processes which are not generally applicable to conventional thermosets.

It can thus be shaped by applying stresses of about from 1 to 10 MPa without however flowing under its own weight.

Likewise, this object can be deformed at a temperature above the temperature Tg, then in a second step, the internal stresses can be eliminated at a higher temperature.

The low viscosity of these objects at these temperatures allows in particular injection or molding under a press. It should be noted that no depolymerization is observed at high temperatures and the objects of the invention retain their crosslinked structure. This property allows the repair of an object of the invention that would be fractured into at least two parts by simple welding of these parts to one another. No mold is required to maintain the shape of the objects of the invention during the repair process at high temperatures. Likewise, an object of the invention can be transformed by application of a mechanical stress to just one part of the object without recourse to a mold, since the objects of the invention do not flow. However, large objects, which have a further tendency to sag, may be held by a frame, such as for glasswork.

Thus, the object as described above can be deformed according to a process comprising the application to the object of a mechanical stress at a temperature (T) above the temperature Tg. The assembly, welding, repair and recycling constitute a particular case of this deformation process. Preferably, in order to allow deformation in a period of time compatible with an industrial application, the deformation process comprises the application to the object of the invention of a mechanical stress at a temperature (T) above the glass transition temperature Tg of the thermoset resin that it contains.

Usually, such a deformation process is followed by a step of cooling to ambient temperature, optionally with application of at least one mechanical stress. For the purposes of the present invention, the term "mechanical stress" is intended to mean the application of a mechanical force, locally or to all or part of the object, this mechanical force aiming to form or deform the object. Among the mechanical stresses that can be used, mention may be made of: pressure, molding, blending, extrusion, blowing, injection, stamping, twisting, flexing, tensile stress and shear. It may for example be twisting applied to the object of the invention in the form of a strip. It may be a pressure applied using a plate or a mold on one or more faces of an object of the invention, or stamping of a pattern in a plate or a sheet. It may also be a pressure exerted in parallel on two objects of the invention in contact with one another so as to cause welding of these objects. In the case where the object of the invention consists of granules, the mechanical stress may consist of blending, for example in a mixer or around the screw of an extruder. It may also consist of an injection or extrusion. The mechanical stress may also consist of blowing, which may for example be applied to a sheet of the object of the invention. The mechanical stress may also consist of a multiplicity of distinct stresses, of an identical or different nature, applied simultaneously or successively to all or part of the object of the invention, or locally.

This deformation process may include a step of mixing or agglomerating the object of the invention with one or more additional components chosen from those mentioned above and in particular: polymers, pigments, dyes, fillers, plasticizers, long or short, woven or nonwoven fibers, flame retardants, antioxidants and lubricants.

The increase in the temperature in the deformation process can be carried out by any known means, such as heating by conduction, convection or induction, by spot heating, infrared, microwave or radiant heating. The means for producing an increase in temperature for carrying out the processes of the invention comprise: an oven, a microwave oven, a heating resistor, a flame, an exothermic chemical reaction, a laser beam, an iron, a hot air gun, an ultrasonic bath, a heated punch, etc. The increase in temperature may optionally be carried out in steps and the duration thereof is adjusted to the expected result.

Although the resin does not flow during its deformation, by virtue of the exchange reactions, by choosing a temperature, a heating time and cooling conditions that are appropriate, the new shape can be free of any residual stress. The object is not therefore weakened or fractured by the application of the mechanical stress. In addition, if the object deformed is subsequently reheated, it will not return to its first shape. This is because the exchange reactions which occur at high temperature promote reorganization of the crosslinking points of the thermoset resin network in such a way as to abolish the mechanical stresses. A sufficient heating time makes it possible to completely abolish these internal mechanical stresses in the object which have been caused by the application of the external mechanical stress.

This method therefore makes it possible to obtain stable complex shapes which are difficult or even impossible to obtain by molding, from simpler elementary shapes. In particular, it is very difficult to obtain, by molding, shapes resulting from twisting. Additionally, the choice of appropriate conditions for temperature, heating time under stress and cooling makes it possible to transform an object of the invention while at the same time controlling the persistence of certain internal mechanical stresses within this object, then, if the object thus transformed is subsequently reheated, a further controlled deformation of this object by controlled release of the stresses can be performed.

Recycling Processes

The object obtained according to the invention can also be recycled:

either by direct treatment of the object: for example, a broken or damaged object of the invention is repaired by means of a deformation process as described above and can thus return to its prior use function or find another function;

or the object is reduced to particles by applying mechanical milling, and the resulting particles are then used in a process for producing an object in accordance with the invention. In particular, according to this process, the particles are simultaneously subjected to an increase in temperature and to a mechanical stress enabling them to be transformed into an object in accordance with the invention.

The mechanical stress which enables the transformation of the particles into an object can for example comprise compression in a mold, blending, and/or extrusion.

This method makes it possible in particular, by application of a sufficient temperature and of an appropriate mechanical stress, to mold new objects from the objects of the invention.

Another advantage of the invention is that it makes it possible to produce objects based on thermoset resin from solid raw materials. These solid raw materials are thus objects according to the invention in the form of parts, of an elementary unit or of a set of elementary units.

The term "elementary units" is intended to mean parts which have a shape and/or an appearance suitable for their subsequent transformation into an object, for instance: particles, granules, balls, sticks, plates, sheets, films, strips, rods, tubes, etc.

The term "set of elementary units" is intended to mean at least 2 elementary units, for example at least 3, at least 5, at least 10 or even at least 100 elementary units. Any process known to those skilled in the art may be used for this purpose. These elementary parts are then transformable, under the combined action of heat and a mechanical stress, into objects of the desired shape: for example, strips can by stamping be cut into smaller parts of chosen shape, sheets can be superimposed and assembled by compression. These thermoset resin-based elementary parts can be more easily stored, transported and handled than the liquid formulations from which they are derived. This is because the step of transforming the elementary parts in accordance with the invention can be carried out by the final user without chemistry equipment (non-toxicity, no expiration date, no VOC, no weighing out of reagents).

One particular case of the deformation process already described thus comprises:

a) the use, as raw material, of an object of the invention in the form of an elementary unit or of a set of elementary units, b) the simultaneous application of a mechanical stress and of an increase in temperature so as to form the object in order to produce a new object, c) the cooling of the object resulting from step b).

Another advantage of this process is that it enables the recycling of the new object produced, it being possible for said object to be reconditioned in the form of elementary units or parts that can in turn be re-formed, in accordance with the invention.

The process of recycling an object of the invention can comprise:

a) the use of an object of the invention as raw material, b) the application of a mechanical stress and optionally of a simultaneous increase in temperature so as to transform this object into a set of elementary units, c) the cooling of this set of elementary units.

Applications

The fields of application of the present invention are mainly those of thermosetting resins, in particular those of epoxy resins, in particular the motor vehicle industry (which groups together any type of motorized vehicle, including heavy goods vehicles), aeronautics, the nautical field, aerospace, sport, construction, the electrical field, electrical insulation, electronics, wind power, packaging and printing.

The compositions, materials and objects of the invention may for example be incorporated into formulations, in particular with typical additives such as fillers, antioxidants, flame retardants, UV protectors, pigments or dyes. The formulations may for example be used for the coating of paper, and the production of inks and paints. The materials or objects of the invention can be used in the form of powders or granules, or else be incorporated into composite materials, in particular those comprising glass fibers, carbon fibers, aramid fibers or fibers of plant origin (flax fibers, hemp fibers, etc.). These fibers may be woven or nonwoven, long fibers or short fibers. The compositions of the invention may also be applied as coatings, for example as varnishes for protection of metals, protection of pipes, protection of floorings.

The compositions of the invention may also be used to produce adhesives, advantageously those which are thermo-crosslinkable or photo-crosslinkable, to encapsulate connectors (it being possible for the composition of the invention to be applied by potting or injection), to produce electrical insulator parts or else to produce prototypes.

FIGURES

EXAMPLES

The following examples illustrate the invention without limiting it.

Characterization Methods

Nuclear magnetic resonance analysis: All the nuclear magnetic resonance (NMR) analyses were carried out on an apparatus with a resonant frequency at 400 MHz, with chloroform as deuterated solvent and at concentrations of 8 mg/ml.

Thermal analysis: the Tg of the samples of examples 2 to 4 was characterized by differential scanning calorimetry (DSC) analysis. The following protocol was applied: first heating at 10° C./min from −70° C. to 170° C., isotherm of 5 min at 170° C., cooling at −10° C./min down to −70° C., isotherm at −70° C. for 5 min, then second heating up to 170° C. at 10° C./min.

Mechanical analysis: the storage moduli (G') of the samples of examples 2 to 4 were measured by dynamic mechanical analysis (DMA) in 3-point flexural geometry. The following protocol was applied: Oscillation amplitude of 25 μm, frequency 1 Hz, starting temperature at −25° C., final temperature at 200° C., heating at 3° C./min. The tests were carried out on samples 30 mm×13 mm×1.5 mm in size.

The samples of examples 5 to 8 were also subjected to a DMA analysis, under slightly different conditions. Specifically, a bar 10×30×3 mm in size was fixed between two clamps and subjected to a rectangular torsion (imposed deformation of 0.05%) in an RDA3 apparatus from Rheometric Scientific, with a frequency of 1 Hz, by carrying out a temperature sweep from 25 to 250° C. with a temperature ramp of 3° C./min. The value of Tα was determined at the top of the peak of the tan δ curve, and is considered hereinafter to be the Tg of the sample, while the storage modulus G' was determined on the rubbery plateau at 200° C.

Example 1

Preparation of a Catalyst According to the Invention, and Characterization Thereof This example illustrates the synthesis of an organometallic titanium complex, used as catalyst according to the invention.

The reaction scheme is represented below:

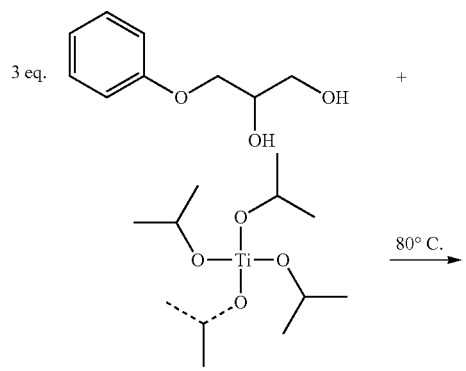

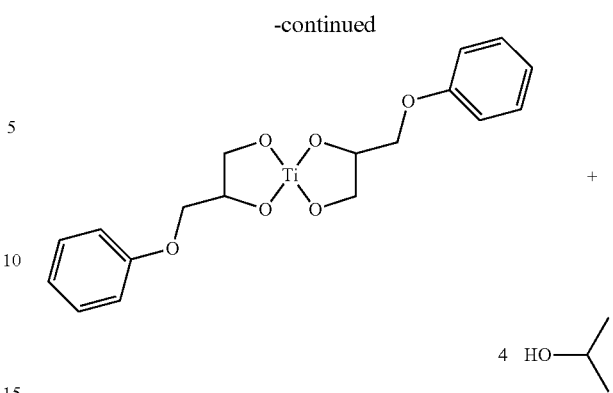

Figure 1:
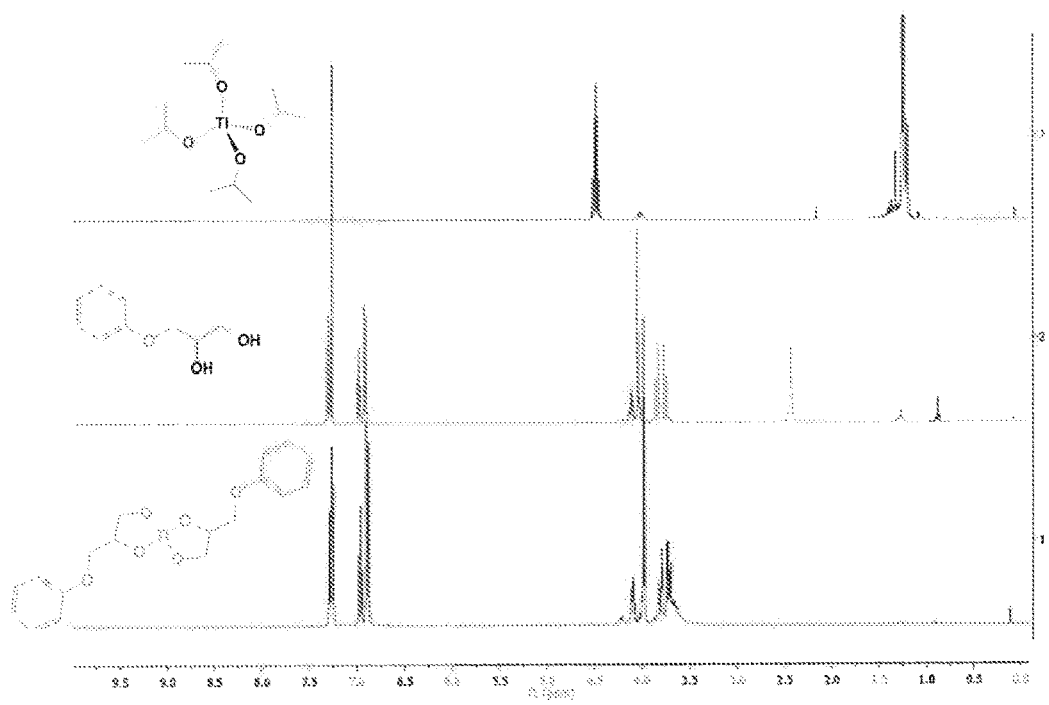
FIG. 1 represents the superimposition of the $^1$H NMR spectra (CDCl$_3$, 400 MHz) of various vitrimer effect catalysts.

The phenoxypropanediol (10 g, 0.06 mol) was placed in a single-necked round-bottomed flask with a volume of 100 ml, then the round-bottomed flask was heated until the reagent was liquid (80° C.) and left to stir for 15 min. Still at 80° C., the titanium isopropoxide (5.63 g, 0.02 mol) was added dropwise, very slowly. The mixture was left to stir for 4 h under an inert atmosphere and then the medium was gradually placed under a dynamic vacuum at 80° C., where it was left for 15 h in order to eliminate the isopropanol. The ligand exchange reaction was virtually instantaneous. During the addition of the titanium isopropoxide, the product precipitated and the reaction medium became white. In order to eliminate the excess ligand, the product at the end of the reaction (in solid form) was placed in an Erlenmeyer flask with 100 ml of chloroform and the mixture was left to stir overnight (phenoxypropanediol is very soluble in chloroform). The product was recovered by filtration and then drying under a dynamic vacuum at 50° C. for 15 h. The final product was characterized by proton NMR (see FIG. 1). It will subsequently be referred to as Ti(PPD)$_2$.

The solubility of the Ti(PPD)$_2$ compound in a DGEBA epoxy resin and in a DGEBA/anhydride system was tested as follows:

Test of Solubility in DGEBA

The DGEBA (DER 330-2.1 g, 12.1 mmol) and Ti(PPD)$_2$ (0.232 g, 0.6 mmol; 5 mol %) are added to a Schlenk tube. The mixture is placed, with stirring, in an oil bath at 130° C. The mixture remains cloudy, since the catalyst is only dispersed and not dissolved.

After 60 min, a sample is taken and analyzed by infrared spectroscopy in order to verify the state of the DGEBA. It is noted that the absorption band corresponding to the epoxide function is still more than 95% intact, indicating that the anionic homopolymerization of the DGEBA is not initiated by the presence of the titanium compound Ti(PPD)$_2$ in the medium at 130° C.

Test of Solubility in the DGEBA+Glutaric Anhydride Reactive Mixture

Glutaric anhydride (0.689 g, 6 mmol; 50 mol %) is added to the above mixture, still with stirring at 130° C. The amount is adjusted such that there are as many epoxide functions as acid functions in the medium (same conditions as during synthesis of a vitrimer plate). The effect is virtually instantaneous, with the total disappearance of catalyst in solid form in the mixture. Said mixture becomes colored and translucent.

The reaction was monitored by infrared spectroscopy showing the drop in the intensity of the absorption band corresponding to the epoxide function (916 cm$^{-1}$), illustrating the progression of the reaction.

Example 2

Synthesis of an Epoxy-anhydride Network in the Presence of 5% of Ti(PPD)$_2$

The following were added to a Teflon beaker: 19 g of epoxy resin of DGEBA type (DER332) in liquid form (DOW, Mass Epoxy Equivalent: 174 g/eq) and 2.1 g of Ti(PPD)$_2$ prepared in example 1 (MW=383.87 g/mol), which corresponded to 0.05 gram atom of titanium per epoxy function. The reagents were mixed while at the same time heating using a hot air gun (T≈60° C.) for 2 mm. The mixture became white, non-translucent. 6.23 g of glutaric anhydride (CAS 108-55-4, MW=114.1 g/mol) in solid form were then added thereto, while heating using a hot air gun (T≈150° C.) until complete dissolution. The mixture was no longer white and became translucent. At that time, it was cast in a mold 100×100×1.4 mm in size (preheated to 140° C.) between two sheets of non-stick siliconized paper, and then fired under a press at 140° C. for 8 h. An infrared spectrum measurement carried out on the material at the end of the reaction demonstrated the complete disappearance of the anhydride (1810 cm$^{-1}$) and epoxy (915 cm$^{-1}$) signals. The band characteristic of ester functions at 1735 cm$^{-1}$ and a broad unresolved absorption peak at 3200-3600 cm$^{-1}$, characteristic of hydroxyl groups, were recorded on the sample after polymerization.

The material exhibited by DMA a Tg of about 70° C., and a storage modulus of 2.2 GPa at 25° C. and of 25 MPa at 150° C.

Figure 5:
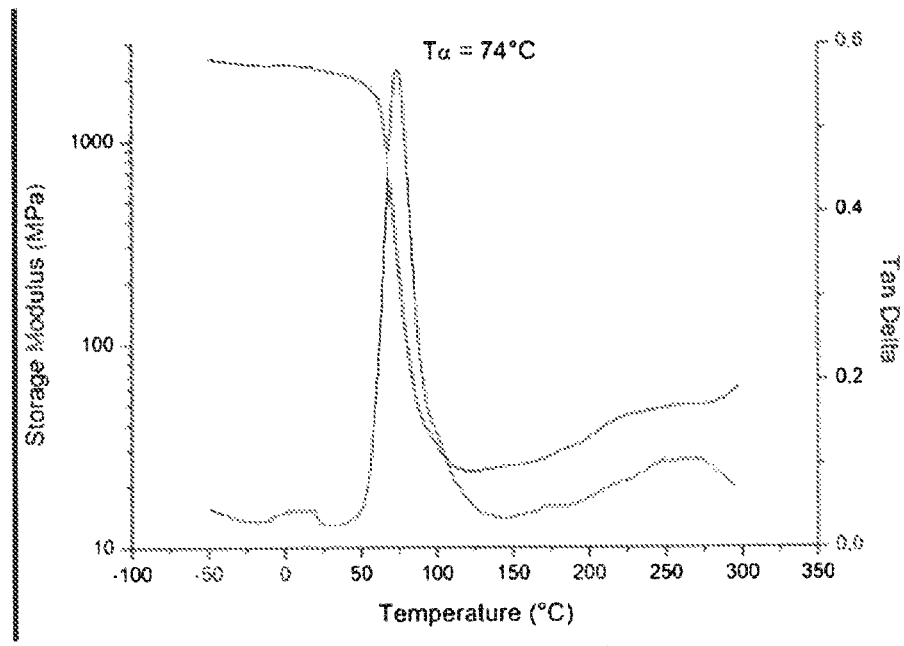
FIG. 5 illustrates the DMA curves of a 1:0.5 DGEBA/glutaric anhydride system with 5 mol % of Ti(PPD)$_2$.

Its DMA curve is shown in FIG. 5. As emerges from this figure, the material exhibits a storage modulus at 25° C. and at 150° C. of 2.2 GPa and of 25 MPa, respectively. The Tα value is 74° C. and the narrowness of the tan delta peak shows that the material is homogeneous.

Figure 4:
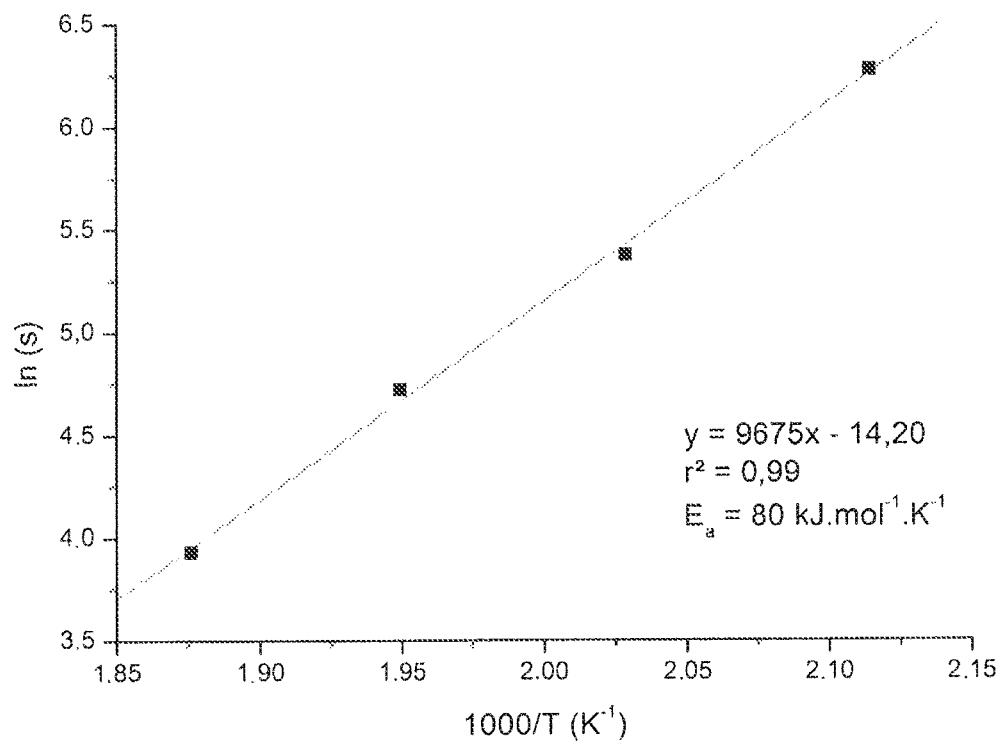
FIG. 4 illustrates the variation in the relaxation time for a DGEBA/glutaric anhydride network catalyzed by 5 mol % of Ti(PPD)$_2$ as a function of the inverse of the temperature.

In addition, FIG. 4 shows the variation in the relaxation time of this material as a function of the inverse of the temperature. As emerges from this figure, the relaxation time follows an Arrhenius law of the type:

$$\frac{1}{\tau} = \frac{1}{\tau_0} e^{-\frac{E_a}{RT}}$$

where $\tau_0$ the normalization constant is a time (s), $E_a$ is the activation energy (J·mol$^{-1}$·K$^{-1}$), R the universal constant of perfect gases (J·mol$^{-1}$), and T the temperature (K). The activation energy, determined from the slope ($E_a/R$), is approximately 80 kJ·mol$^{-1}$·K$^{-1}$.

Comparative Example 3

Synthesis of an Epoxy-anhydride network in the Presence of 5% of Zinc Acetylacetonate

A comparative sample was prepared using the same protocol as in example 2, but using zinc acetylacetonate as catalyst at the same concentration, in other words at 0.05 gram atom of titanium per epoxy function.

The material exhibited by DMA a Tg of about 70° C., and a storage modulus of 2 GPa at 25° C. and of 19 MPa at 150° C.

Example 4

Synthesis of an Epoxy-anhydride Network in the Presence of 5% of Titanium Isopropoxide

A sample was prepared using the same protocol as in example 2, but using titanium isopropoxide (CAS 546-68-9, MW=284.22 g/mol) as catalyst at the same concentration, in other words at 0.05 gram atom of titanium per epoxy function.

The material exhibited by DMA a Tg of about 67° C., and a storage modulus of 2.4 GPa at 25° C. and of 8.5 MPa at 150° C.

Example 5

Synthesis of an Epoxy-anhydride Network in the Presence of 10% of Titanium Isopropoxide

Three samples of vitrimer material (respectively 5a, 5b and 5c) were prepared according to the following method.

Added to a beaker were an epoxy resin of DGEBA type (DER332) in liquid form (DOW, Mass Epoxy Equivalent: 174 g/eq), methyltetrahydrophthalic anhydride (MTHPA) (MW=166.18 g/mol) and titanium isopropoxide (supplied by Dorf Ketal), in a proportion of 0.1 gram atom of titanium per epoxy function. The reagents were mixed and then homogenized in a thermostated oil bath at 100° C. for approximately 10 minutes. The mixture was then cast in a lightly siliconized 70×140×3 mm hollow metal mold. The mold was interlocked, by means of a silicone seal, with a metal plate covered with a Teflon coating, then the assembly was introduced into a heated press preset to a temperature of 140° C. and firing was begun at a pressure of 10 bar. The firing was carried out for 17 hours.

A molar ratio of epoxide functions of the resin to anhydride functions of the curing agent respectively equal to 1/0.8; 1/1 and 1/1.2 was used to produce these samples.

The Tg of the resulting materials was measured by DMA along with the storage modulus of said resulting materials.

These materials exhibited respectively a Tg of 118° C., 116° C. and 102° C. and a storage modulus at 200° C. of 17 MPa, 12.6 MPa and 11.6 MPa.

Comparative Example 6

Synthesis of an Epoxy-anhydride Network in the Presence of 10% of Zinc Acetylacetonate

Three samples of material (respectively 6a, 6b and 6c) were prepared in a manner identical to example 5, except that the catalyst was replaced with zinc acetylacetonate or Zn(acac)$_2$. These materials exhibited respectively a Tg of 138° C., 130° C. and 112° C. and a storage modulus at 200° C. of 16 MPa, 13.5 MPa and 10.2 MPa.

Example 7

Synthesis of an Epoxy-anhydride Network in the Presence of 10% of Titanium Acetylacetonate

A sample of material was prepared in a manner identical to example 5 using a molar ratio of epoxide functions of the resin to anhydride functions of the curing agent equal to 1/0.8, except that the catalyst was replaced with titanium acetylacetonate or Ti(acac)$_2$.

This material exhibited a Tg of 112° C. and a storage modulus at 200° C. of 8.0 MPa.

Example 8

Synthesis of an Epoxy-anhydride Network in the Presence of Titanium Isopropoxide and of an Additional Catalyst of Amine Type

Two samples of vitrimer material were prepared according to a process similar to that described in example 5, the operating conditions of which were modified as described in table 1 below. Additional samples were prepared by adding a variable amount of additional catalyst of amine type, namely either 2-methylimidazole (hereinafter "2-MIA") or 2,4,6-tri(dimethylaminomethyl)phenol (hereinafter "Anc" for Ancamine K54 from Air Products), to the system before curing.

TABLE 1

| | Sample | | | | | |
|---|---|---|---|---|---|---|
| | 8a | 8b | 8c | 8d | 8e | 8f |
| Epoxide | DER332 | DER332 | DER332 | DER332 | DER332 | DER332 |
| Curing agent | MTHPA | MTHPA | MTHPA | MTHPA | MTHPA | MTHPA |
| Additive | — | 2-MIA | 2-MIA | — | Anc | Anc |
| Catalyst | Ti(iPr)$_4$ | Ti(iPr)$_4$ | Ti(iPr)$_4$ | Ti(iPr)$_4$ | Ti(iPr)$_4$ | Ti(iPr)$_4$ |
| mol % amine/epoxy | — | 0.5% | 2.5% | — | 1% | 2% |
| mol % catalyst/epoxy | 5% | 5% | 5% | 10% | 10% | 10% |
| Tg (° C.) | 136 | 122 | 120 | 118 | 108 | 114 |
| G' (MPa) | 17 | 12 | 12 | 17 | 13 | 17 |

Example 9

Study of the Relaxation and Deformation Properties of Various Vitrimer Materials a) The samples of examples 2, 3 and 4 were subjected to a stress relaxation experiment: the stress relaxation times were measured by means of a DMA (or DMTA for Dynamic Mechanical Thermal Analysis) in 3-point flexural geometry. The following protocol was applied: heating up to test temperature, isotherm of 20 min, then application of a 1% deformation. The tests were carried out on samples 30 mm×13 mm×1.4 mm in size.

Figure 3:
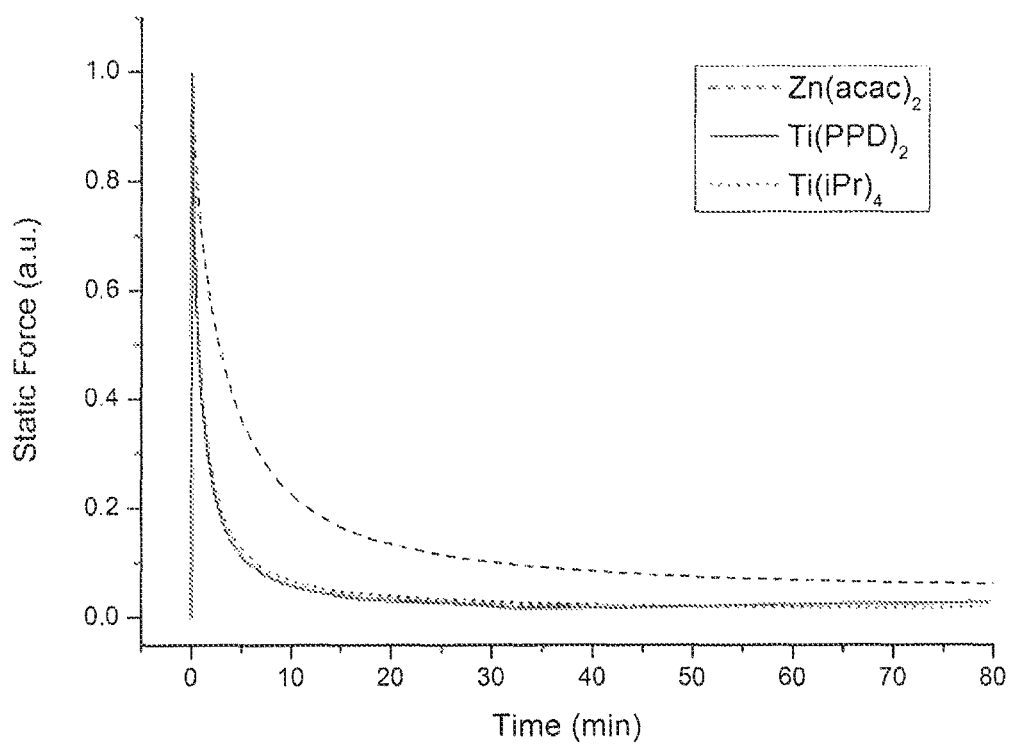
FIG. 3 illustrates the superimposition of the stress relaxations (at 260° C.) of the vitrimers catalyzed by 5 mol % of Ti(iPr)$_4$, and by 5 mol % of Ti(PPD)$_2$ and by 5 mol % of Zn(acac)$_2$. The static force is represented as a function of time.

The results are collated in the appended FIG. 3. As this figure shows, the samples obtained using the catalysts according to the invention exhibit similar performance levels that are much higher than those of the material obtained using zinc acetylacetonate, insofar as their stresses are more completely and more rapidly relaxed.

b) in parallel, each of the samples prepared according to examples 5 to 8 was subjected to an experiment consisting in imposing, on a test specimen of material of 40×20×2 mm, a 3-point flexural deformation under a nitrogen stream, using a Metravib apparatus of DMA50N type, after the sample had been brought to a temperature equal to Tα+100° C. and stabilized for 5 min at this temperature. The change in the stresses induced in the material in order to keep the deformation constant is monitored for 5000 seconds and measured using a sensor. A force equal to zero is then imposed on the sample and the deformation (recovery) of the sample is measured for a further 5000 seconds. When the material retains the deformation that was imposed on it, it is considered that all the stresses have been relaxed. The normalized stress (σ/σo) is then plotted as a function of time and, for each test, the relaxation time required to obtain a normalized stress value equal to 1/e, and also the percentage of stresses relaxed at 5000 seconds, hereinafter denoted σ$_{5000s}$, are recorded.

The results obtained are collated in table 2 below.

TABLE 2

| | Sample | | | | | | |
|---|---|---|---|---|---|---|---|
| | 5a | 5b | 5c | 6a comp | 6b comp | 6c comp | 7 |
| τ (s) | 75 | 510 | 370 | 1105 | 1565 | 3630 | 555 |
| σ$_{5000 s}$ (%) | 100 | 100 | 100 | 100 | 84 | 69 | 100 |

TABLE 2-continued

| | Sample | | | | | |
|---|---|---|---|---|---|---|
| | 8a | 8b | 8c | 8d | 8e | 8f |
| τ (s) | 2430 | 1060 | 735 | 75 | 45 | 23 |
| σ$_{5000 s}$ (%) | 75 | 85 | 100 | 100 | 100 | 100 |

As emerges from this table, the catalysts according to the invention (samples 5a to 5c and 7) make it possible to obtain materials capable of relaxing their stresses more completely and more rapidly than the materials obtained using the same amount of zinc acetylacetonate-based catalyst (samples 6a to 6c). Moreover, these performance levels are not obtained to the detriment of the mechanical properties of the material. In addition, these performance levels of the catalysts according to the invention are further improved in the presence of an additional catalyst of amine type, as shown by the comparison of samples 8b and 8c with sample 8a and of samples 8e and 8f with sample 8d.

Example 10

Study of the Thermal Stability of Various Vitrimer Materials a) The samples of examples 2, 3 and 4 were subjected to a thermogravimetric analysis (TGA). 10 mg of product (catalyst or resin) were placed in an alumina capsule. The gravimetric measurements were carried out from 25° C. to 900° C., at 10° C./min.

The samples obtained using the catalysts according to the invention are more stable than those using zinc acetylacetonate, in a range of temperatures suitable for their industrial transformation, i.e. up to a temperature of approximately 200° C. The Ti(PPD)$_2$-based catalyst is even stable above this temperature and does not substantially degrade up to 300° C.

Figure 2:
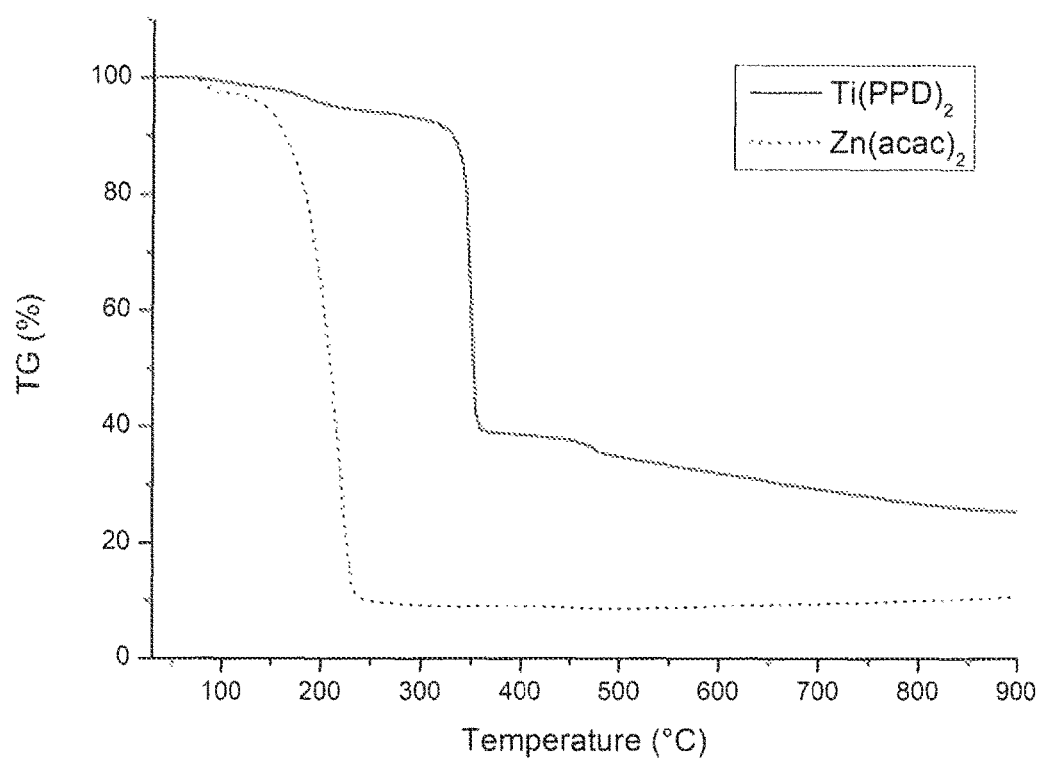
FIG. 2 represents the superimposition of the TGA curves of the Zn(acac)$_2$ catalyst and of the Ti(PPD)$_2$ catalyst.

In particular, it was observed that the material of example 2 showed a loss of mass of only 0.07% at 260° C., whereas the material of comparative example 3 showed a loss of mass of 1.68% at the same temperature.

b) The appended FIG. 2 shows that the Zn(acac)$_2$ catalyst is less thermally stable than the Ti(PPD)$_2$ catalyst since it degrades starting from 200° C., whereas the latter undergoes only a small loss of mass up to 300° C.

c) The thermal stability of the materials of examples 5a and 6a and also of example 2 were moreover evaluated by TGA on a Perkin Elmer apparatus of type TGA7, while performing a temperature scan from 25° C. to 500° C. according to a ramp of 10° C./min. The temperature resulting in a loss of material of 1% was 176° C. in the case of the material of comparative example 6a and 235° C. in the case of the material of example 5a, thereby confirming the better thermal resistance of the materials according to the invention at the re-forming and recycling temperatures.

The temperature resulting in a loss of material of 1% was 254° C. in the case of the material of example 2 prepared with Ti(PPD)$_2$.

The invention claimed is:

1. A composition comprising at least:
   a catalyst comprising titanium bis(3-phenoxy-1,2-propane dioxide) (Ti(PPD)$_2$),
   a thermosetting resin comprising at least one epoxide function and optionally at least one free hydroxyl and/or ester function, and
   a thermosetting-resin curing agent selected from carboxylic acid anhydrides,
   wherein the thermosetting resin is selected from the group consisting of glycidyl esters, glycidyl ethers, glycidyl amines and glycidyl isocyanurates, comprising at least two glycidyl groups per molecule, and epoxidized olefin compounds which are linear, branched or cyclic comprising more than six members.

2. The composition as claimed in claim 1, wherein the catalyst further comprises titanium isopropoxide.

3. The composition as claimed in claim 1, wherein the thermosetting resin is selected from the group consisting of glycidyl esters, glycidyl ethers, glycidyl amines and glycidyl isocyanurates, comprising at least two glycidyl groups per molecule, and mixtures thereof.

4. The composition as claimed in claim 1, wherein the thermosetting resin is selected from the group consisting of epoxidized olefin compounds which are linear, branched or cyclic comprising more than six members, and mixtures thereof.

5. The composition as claimed in claim 1, wherein the thermosetting resin is selected from the group consisting of: bisphenol A diglycidyl ether (DGEBA), tetraglycidyl methylene dianiline (TGMDA), bisphenol F diglycidyl ether, Novolac resins, trimethylol triglycidyl ether (TMPTGE), the diglycidyl ester of phthalic, isophthalic or terephthalic acid, tetrabromo bisphenol A diglycidyl ether, 1,4-butanediol diglycidyl ether, the epoxidized cycloaliphatic resin represented by formula (II), triglycidyl isocyanurate (TGIC), poly(glycidyl methacrylate), and mixtures thereof

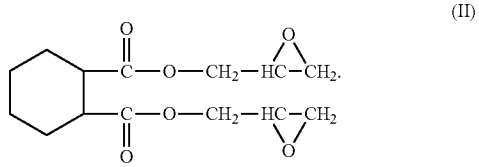 [SMILES: O=C(OCC1CO1)C1CCCCC1C(=O)OCC1CO1]

(II)

6. The composition as claimed in claim 1, wherein the thermosetting resin is selected from the group consisting of bisphenol A diglycidyl ether (DGEBA), tetraglycidyl methylene dianiline (TGMDA), Novolac resins and glycidyl methacrylate.

7. The composition as claimed in claim 1, wherein the amount of curing agent is such that the number of moles of epoxide functions of the thermosetting resin ranges from 50% to 300%, relative to the number of moles of anhydride functions of the curing agent.

8. The composition as claimed in claim 1, wherein the content of thermosetting resin and of curing agent ranges from 10% to 90% by weight, relative to the total weight of the composition, the remainder to 100% being provided by the catalyst and optionally by one or more additional compounds selected from the group consisting of:
   polymers, pigments, dyes, fillers, plasticizers, long or short fibers, woven or nonwoven fibers, flame retardants, antioxidants, lubricants, wood, glass, metals, and mixtures thereof.

9. The composition as claimed in claim 1, further comprising at least one epoxide-opening additional catalyst.

10. The composition as claimed in claim 1, further comprising at least one polyol.

11. The composition as claimed in claim 10, wherein the polyol is glycerol, trimethylolpropane or pentaerythritol.

12. The composition as claimed in claim 1, comprising at least one thermosetting resin selected from the group consisting of bisphenol A diglycidyl ether (DGEBA), tetraglycidyl methylene dianiline (TGMDA), Novolac resins, and glycidyl methacrylate, and at least one carboxylic acid anhydride.

13. A kit for producing a composition as claimed in claim 1, comprising at least:
    a first composition comprising the catalyst;
    a second composition comprising the curing agent; and
    a third composition comprising the thermosetting resin.

14. A method for producing an object made of thermoset resin that is hot-deformable, comprising using the composition as claimed in claim 1.

15. An object comprising a thermoset resin obtained from a composition as defined in claim 1.

16. A process for deforming an object, comprising applying to an object in accordance with claim 15 a mechanical stress at a temperature (T) above the glass transition temperature Tg of the thermoset resin.

17. The composition as claimed in claim 1, wherein the thermosetting resin is a glycidyl ether.

18. A kit for producing a composition as claimed in claim 1, comprising:
    a first composition comprising the catalyst and the curing agent; and
    a second composition comprising the thermosetting resin.

19. A kit for producing a composition as claimed in claim 1, comprising:
    a first composition comprising the catalyst and the thermosetting resin; and
    a second composition comprising the curing agent.

20. A method of producing a composition as claimed in claim 1, comprising combining the catalyst, the thermosetting resin, and the curing agent.

21. An organometallic titanium complex corresponding to the structure titanium bis(3-phenoxy-1,2-propane dioxide) (Ti(PPD)$_2$).

22. A method comprising using the organometallic titanium complex as claimed in claim 21 as a vitrimer effect catalyst in a system based on an epoxy resin and on a curing agent of anhydride type.

* * * * *